US012029576B2

(12) United States Patent
Hecox

(10) Patent No.: US 12,029,576 B2
(45) Date of Patent: *Jul. 9, 2024

(54) SYSTEMS AND METHODS FOR SEIZURE DETECTION BASED ON CHANGES IN ELECTROENCEPHALOGRAM (EEG) NON-LINEARITIES

(71) Applicant: Advanced Global Clinical Solutions Inc., New Berlin, WI (US)

(72) Inventor: Kurt E. Hecox, New Berlin, WI (US)

(73) Assignee: Advanced Global Clinical Solutions Inc., New Berlin, WI (US)

( * ) Notice: Subject to any disclaimer, the term of this patent is extended or adjusted under 35 U.S.C. 154(b) by 241 days.

This patent is subject to a terminal disclaimer.

(21) Appl. No.: 17/366,854

(22) Filed: Jul. 2, 2021

(65) Prior Publication Data

US 2021/0330243 A1 Oct. 28, 2021

Related U.S. Application Data

(63) Continuation of application No. 16/938,501, filed on Jul. 24, 2020, now Pat. No. 11,083,409, and a (Continued)

(51) Int. Cl.
*A61B 5/00* (2006.01)
*A61B 5/30* (2021.01)
(Continued)

(52) U.S. Cl.
CPC .......... *A61B 5/4094* (2013.01); *A61B 5/0006* (2013.01); *A61B 5/002* (2013.01);
(Continued)

(58) Field of Classification Search
None
See application file for complete search history.

(56) References Cited

U.S. PATENT DOCUMENTS

| 3,863,625 A | 2/1975 | Viglione et al. |
| 4,566,464 A | 1/1986 | Piccone et al. |
| (Continued) | | |

FOREIGN PATENT DOCUMENTS

| JP | 2017-042562 | 7/2017 |
| KR | 100425532 B1 | 3/2004 |
| (Continued) | | |

OTHER PUBLICATIONS

Extended European Search Report regarding European Application No. 20854632.5, dated Nov. 8, 2022, 10 pps.

(Continued)

*Primary Examiner* — Etsub D Berhanu
(74) *Attorney, Agent, or Firm* — Foley & Lardner LLP

(57) ABSTRACT

A seizure detection system including one or more circuits, the one or more circuits configured to receive an electroencephalogram (EEG) signal generated based on electrical brain activity of a patient and determine different types of metrics based on the EEG signal, the different types of metrics indicating non-linear features of the EEG signal. The one or more circuits are configured to determine whether one or more of the different types of metrics exhibit changes over time that meet a predefined level of statistical significance, generate a user interface, the user interface including a real-time trend of the EEG signal and the one or more of the different types of metrics, and cause a user interface device to display the user interface.

8 Claims, 5 Drawing Sheets

Related U.S. Application Data continuation of application No. 16/938,541, filed on Jul. 24, 2020, now Pat. No. 11,076,799, which is a continuation of application No. PCT/US2020/025136, filed on Mar. 27, 2020, said application No. 16/938,501 is a continuation of application No. PCT/US2020/025136, filed on Mar. 27, 2020.

(60) Provisional application No. 62/890,497, filed on Aug. 22, 2019.

(51) Int. Cl.
　　*A61B 5/316*　　　(2021.01)
　　*A61B 5/369*　　　(2021.01)
　　*A61B 5/372*　　　(2021.01)
　　*G16H 50/20*　　　(2018.01)

(52) U.S. Cl.
　　CPC .............. *A61B 5/0022* (2013.01); *A61B 5/30* (2021.01); *A61B 5/316* (2021.01); *A61B 5/369* (2021.01); *A61B 5/372* (2021.01); *A61B 5/7203* (2013.01); *A61B 5/742* (2013.01); *A61B 5/746* (2013.01); *G16H 50/20* (2018.01); *A61B 2503/045* (2013.01)

(56) References Cited

U.S. PATENT DOCUMENTS

| | | | |
|---|---|---|---|
| 5,743,860 | A | 4/1998 | Hively et al. |
| 5,815,413 | A | 9/1998 | Hively et al. |
| 5,857,978 | A | 1/1999 | Hively et al. |
| 6,011,990 | A | 1/2000 | Schultz et al. |
| 6,304,775 | B1 | 10/2001 | Iasemidis et al. |
| 6,658,287 | B1 | 12/2003 | Litt et al. |
| 2002/0035338 | A1 | 3/2002 | Dear et al. |
| 2002/0095099 | A1 | 7/2002 | Quyen et al. |
| 2006/0200038 | A1 | 9/2006 | Savit et al. |
| 2009/0124923 | A1 | 5/2009 | Sackellares et al. |
| 2012/0197092 | A1 | 8/2012 | Luo et al. |
| 2013/0096840 | A1 | 4/2013 | Osorio et al. |
| 2014/0194769 | A1* | 7/2014 | Nierenberg .......... A61B 5/4094 600/544 |
| 2015/0126892 | A1* | 5/2015 | Kim ...................... A61B 5/168 600/545 |
| 2015/0282755 | A1 | 10/2015 | Deriche et al. |
| 2017/0035316 | A1 | 2/2017 | Kuzniecky et al. |
| 2017/0231519 | A1 | 8/2017 | Westover et al. |
| 2017/0245804 | A1 | 8/2017 | Watanabe et al. |
| 2017/0258410 | A1 | 9/2017 | Gras |
| 2017/0311870 | A1 | 11/2017 | Bardakjian et al. |
| 2019/0209072 | A1 | 7/2019 | Shafique et al. |

FOREIGN PATENT DOCUMENTS

| | | |
|---|---|---|
| WO | WO-2016/013596 | 4/2017 |
| WO | WO-2017/145226 | 6/2018 |

OTHER PUBLICATIONS

Yuan Ye et al: "A Comparison Analysis of Embedding Dimensions between Normal and Epileptic EEG Time Series", Journal of Physiological Sciences, vol. 58, No. 4, Jan. 1, 2008 (Jan. 1, 2008), pp. 239-247, XP055976529 JP.

Celka, P, et al., Time-varying statistical complexity measures with application to EEG analysis and segmentation, 2001 Conference Proceedings of the 23rd Annual International Conference of the IEEE Engineering in Medicine and Biology Society, 2001, vol. 2, pp. 1919-1922.

Yuan, Y. et al., Automated Detection of Epileptic Seizure Using Artificial Neural Network, 2008 2nd International Conference on Bioinformatics and Biomedical Engineering, 2008, pp. 1959-1962.

Abasolo, D. et al., "Non-Linear Analysis of Intracranial Electroencephalogram Recordings with Approximate Entropy and Lempel-Ziv Complexity for Epileptic Seizure Detection," Proceedings of the 28th Annual International Conference of the IEEE EMBS, Cit? Internationale, Lyon, France, Aug. 23-26, 2007, pp. 1953-1956.

Akbarian, B. et al., "Automatic Seizure Detetion Based on Nonlinear Dynamical Analysis of EEG Signals and Mutual Information," Basic and Clinical Neuroscience, Jul., Aug. 2018, vol. 9, No. 4, pp. 227-240.

Anticipation of epileptic seizures from standard EEG recordings, The Lancet, vol. 361, Mar. 15, 2003, www.thelancet.com, p. 970.

Bedeeuzzaman, M et al., "Automatic Seizure Detection Using Inter Quartile Range," International Journal of Computer Applications (0975-8887), vol. 44, No. 11, Apr. 2012, pp. 1-6.

Bergey, G.K., et al., "Epileptic Seizures are Characterized by Changing Signal Complexity," Clin Neurophysiol, Feb. 2001;112(2):241-9, 1 page.

Burns, Samuel P. et al., "A Network Analysis of the Dynamics of Seizure," 34th Annual International Conference of the IEE EMBS, San Diego, California USA, Aug. 28-Sep. 1, 2012, pp. 4684-4697.

Chillemi et al. Early Trends in Seizure Onset: A Nonlinear Approach. In: D'Attellis CE, Kluev VV, Mastrorakis NE, editors. Mathematics and computers in science and engineering. Word Scientific and Engineering Society Press; 2001. p. 156-60. (Year: 2001).

Ghosh, A. et al., "Pre-ictal Epileptic Seizure Prediction Based on ECG Signal Analysis," 2017 2nd International Conference for Convergence in Techology (12CT), pp. 920-925.

Hills, "Seizure detection using FFT, temporal and spectral correlation coefficients, eigenvalues and Random Forest," retrieved from https://www.kaggle.com/blobs/download/forum-message-attachment-files/4803/seizure-detection.pdf (2014).

International Search Report and Written Opinion regarding Appl. No. PCT/US2020/025136, dated Jun. 16, 2020.

Lehnertz et al. Can Epileptic Seizures be Predicted? Evidence from Nonlinear Time Series Analysis of Brain Electrical Activity. Physical Review Letters, vol. 80, No. 22, Jun. 1, 1998. (Year: 1998).

Lehnertz et al. Seizure prediction by nonlinear EEG analysis. IEEE Engineering in Medicine and Biology Magazine, Jan. 2003. (Year: 2003).

Lehnertz, K., "Non-Linear Time Series Analysis of Intracranial EEG Recordings in Patients With Epilepsy—An Overview," International Journal of Psychophysiology 34 (1999) pp. 45-52.

Lehnertz, Klaus et al., "Nonlinear EEG Analysis in Epilepsy: Its Possible Use for Interictal Focus Localization, Seizure Anticipation, and Prevention," Journal of Clinical Neurophysiology, 18(3):209-222, 2001 American Clinical Neurophysiology Society.

Lehnertz. Epilepsy and Nonlinear Dynamics. J Biol Phys (2008) 34:253-266. (Year: 2008).

Liang, Z. et al., "EEG Entropy Measures in Anesthesia," Frontiers in Computational Neuroscience, vol. 9, Article 16, 17 pages, published Feb. 18, 2015, doi: 10.3389/fncom.2015.00016.

Martinerie et al. Epileptic seizures can be anticipated by non-linear analysis. Natural Medicine, vol. 4, No. 10, Oct. 1998 (Year: 1998).

Natus NeuroWorks EEG Solutions, PN 024991, Rev 01, 4 pps., located at website: https://partners.natus.com/asset/resource/file/neuro/asset/2018-07/024991_01%20NeuroWorks%20EEG%20Solutions%20Brochure%20fnl.pdf (2008).

Persyst, "Persyst 13 Overview," located at https://www.youtube.com/watch?v=vVmHQIZ3x-Y, Nov. 30, 2016.

Persyst, "Seizure Detection," retrieved from https://www.persyst.com/technology/seizure-detection/ in Jul. 2020 (undated).

Schelter et al. Testing statistical significance of multivariate time series analysis techniques for epileptic seizure prediction. Chaos 16, 013108 (2006). (Year: 2006).

Schindler, et al., "Assessing seizure dynamics by analysing the correlation structure of multichannel intracranial EEG," Brain 130(1), pp. 64-77 (2007).

Schindler, et al., "Increasing synchronization may promote seizure termination: Evidence from status epilepticus," Clinical Neurophysiology 118(9), pp. 1955-1968 (2007).

(56) References Cited

OTHER PUBLICATIONS

Senger & Tetzlaff, "Eigenvalue based EEG signal analysis for seizure prediction," Sixth International Workshop on Seizure Prediction, retrieved from https://www.iwsp4.org/IWSP6_Program_Booklet.pdf, p. 35 (2013).

Senger & Tetzlaff, "New Signal Processing Methods for the Development of Seizure Warning Devices in Epilepsy," IEEE Transactions on Circuits and Systems I: Regular Papers 63(5), pp. 609-616 (2016).

Song, Yuedong, "A review of developments of EEG-based automatic medical support systems for epilepsy diagnosis and seizure detection," J. Biomedical Science and Engineering, 2011, 4, pp. 788-796. doi: 10.4236/jbise.2011.412097 Published Online Dec. 2011 (http://www.SciRP.org/journal/jbise/).

Van Der Heyden, M.J., et al., "Non-Linear Analysis of Intracranial Human EEG in Temporal Lobe Epilepsy," Clinical Neurophysiology, vol. 110, Issue 10, 2 pages (1999).

Van Drongelen, W., "Seizure Anticipation in Pediatric Epilepsy: Use of Kolmogorov Entropy," Pediatr Neurol. Sep. 2003, 29(3): pp. 207-213.

Wang, et al., "Feature extraction and recognition of epileptiform activity in EEG by combining PCA with ApEn," Cognitive Neurodynamics 4, pp. 233-240 (2010).

Williamson, James R. et al., "Epileptic Seizure Prediction Using the Spatiotemporal Correlation structure of Intracranial EEG," ICASSP 2011, 978-1-4577-0539-7/11, pp. 665-668.

Winterhalder et al. The seizure prediction characteristic: a general framework to assess and compare seizure prediction methods. Epilepsy & Behavior 4 (2003) 318-325. (Year: 2003).

Yadollahpour, A. et al., "Seizure Prediction Methods: A Review of the Current Predicting Techniques," Biomedical & Pharmacology Journal, vol. 7, No. 1, 2014, pp. 153-162.

Yakovlevea, et al., "EEG Analysis in Structural Focal Epilepsy Using the Methods of Nonlinear Dynamics (Lyapunov Exponents, Lempel-Ziv Complexity, and Multiscale Entropy)," Thee Scientific World Journal 2020, 8407872, 13 pages (2020).

\* cited by examiner

SYSTEMS AND METHODS FOR SEIZURE DETECTION BASED ON CHANGES IN ELECTROENCEPHALOGRAM (EEG) NON-LINEARITIES

CROSS-REFERENCE TO RELATED PATENT APPLICATIONS

This application is a continuation of U.S. patent application Ser. No. 16/938,541 filed Jul. 24, 2020, which is a continuation of P.C.T. Application No. PCT/US2020/025136 filed Mar. 27, 2020 which claims the benefit of and priority to U.S. Provisional Patent Application No. 62/890,497 filed Aug. 22, 2019. This application is also a continuation of U.S. patent application Ser. No. 16/938,501 filed Jul. 24, 2020, which is a continuation of P.C.T. Application No. PCT/US2020/025136 filed Mar. 27, 2020 which claims the benefit of and priority to U.S. Provisional Patent Application No. 62/890,497 filed Aug. 22, 2019. The entirety of each of these applications is incorporated by reference herein.

BACKGROUND

The present disclosure relates generally to electroencephalogram (EEG) analysis. More particularly, the present disclosure relates to EEG analysis for seizure detection in a patient.

Seizures occur commonly in patients with a wide range of medical issues. Seizures afflict more than fifty million persons worldwide. In some cases, seizures may be benign but in an extreme form, a seizure can be life threatening. Accordingly, it is important to detect and respond to seizures. The earlier seizures are detected and treated, the better the outcome for the patient. However, detecting a seizure may be challenging since there may be no visible signs that a seizure is occurring in a patient. In particular, it may be difficult to visually detect that a patient in intensive care or a young patient (a child or infant) are experiencing a seizure.

Accordingly, often, a record of EEG data may be collected for such a patient for analysis by an epileptologist, in some cases, up to twenty-four hours of continuous EEG data recording may be necessary for manual analysis by the epileptologist. Manual analysis of such a large amount of data may be cumbersome, time consuming, and expensive. Some EEG analytics algorithms for seizure detection exist, however, these algorithms have low performance in young children. For example, some seizure detection algorithms may reach detection rates of 80% in adults but only attain detection rates of 50-60% in young children. Furthermore, such algorithms may also have a large number of false positive rates, in some cases, more than 100 false positives per day for a single patient when the patient is a young child. This number of false positives requires manual review for all records of a child and as the analysis algorithms do not appropriately reduce the amount of manual EEG data review required. Part of the failure of such EEG detection algorithms in children is due to the high variability in the nature of the abnormal EEG waveforms recorded for children.

SUMMARY

One implementation of the present disclosure is a seizure detection system including one or more circuits. The one or more circuits are configured to receive an electroencephalogram (EEG) signal generated based on electrical brain activity of a patient. The one or more circuits are configured to determine metrics based on the EEG signal. The metrics indicate non-linear features of the EEG signal. The one or more circuits are configured to determine that the EEG signal indicates a candidate seizure by determining, based at least in part on the metrics, a change in the non-linear features of the EEG signal over time, and generate a seizure alert indicating that the EEG signal may indicate a candidate seizure. A "candidate seizure," as used herein, may refer to any seizure, epileptic discharge, sub-clinical event, potential seizure for technician review, or the like. The change in the non-linear features indicates a physiological force that gives rise to the candidate seizure. The time between an occurrence of the change in the non-linear features and an occurrence of the candidate seizure may vary.

In some embodiments, the processing circuit is configured to determine that the EEG signal indicates the candidate seizure based on at least one of a default parameter value or a user defined parameter value.

In some embodiments, the seizure detection system is a cloud-based system, wherein the one or more circuits are configured to receive the EEG signal from a local EEG acquisition system via a network and provide result data to the local EEG acquisition system via the network.

In some embodiments, the seizure detection system is a local system. In some embodiments, the local system is integrated with a local EEG system or connected locally to an EEG acquisition system.

In some embodiments, determining, based at least in part on the metrics, the change in the non-linear features of the EEG signal includes determining an increase in the non-linear features over time. In some embodiments, the method includes determining an overall change of the non-linear features (e.g., values indicating how much the non-linear features have changed). In some embodiments, the method includes determining an overall increase or overall decrease of the non-linear features (e.g., in each of the non-linear features) over a time period. In some embodiments, the method includes determining whether a trajectory of the non-linear features increases or decreases over the time period.

In some embodiments, the metrics include at least one of dimensionality, synchrony, Lyapunov exponents, entropy, global non-linearity, distance differences between recurrence trajectories, self-similarity, or eigenvalues.

In some embodiments, the one or more circuits are configured to determine that the EEG signal indicates a seizure alert by determining, based at least in part on the metrics, the change in the non-linear features of the EEG signal over time by performing a preliminary analysis with one of the metrics, wherein the preliminary analysis indicates that the EEG signal indicates the candidate seizure or that the EEG signal includes noise and performing a secondary analysis with one or more metrics of the metrics to determine whether the EEG signal indicates the candidate seizure or that the EEG signal includes the noise and/or other artifacts.

In some embodiments, the one or more circuits are configured to determine probabilities of a trajectory of each of the plurality of metrics at a plurality of points in time and determine whether the trajectory of each of the plurality of metrics is significant based on the probabilities. In some embodiments, determining, based at least in part on the plurality of metrics, the change in the non-linear features of the EEG signal includes mapping significant metrics of the plurality of metrics to a category, wherein the category results in a seizure alert. In some embodiments, determining the change in the non-linear features may include determining a trajectory of the non-linear features. A trajectory may be a pattern of change in a metric over time. The trajectory can be determined for a metric by plotting values (or recording values) of the metric. In some embodiments, determining the trajectory includes plotting values of the metric in phase space and determining the trajectory of the metric from the phase space plot.

In some embodiments, the one or more circuits are configured to determine a dimensionality of the EEG signal by performing a phase space analysis by increasing a value of the dimensionality until a number of false neighbors reaches zero, wherein a starting value of the dimensionality is based on an age of the patient.

In some embodiments, the one or more circuits are configured to determine whether one or more of the metrics exhibit statistically significant changes over time and generate a user interface. In some embodiments, the user interface includes a real-time trend of the EEG signal and the one or more of the metrics. In some embodiments, the one or more circuits are configured to cause a user interface device to display the user interface.

In some embodiments, one of the metrics is an eigenvalue, wherein the user interface further includes a trend of the eigenvalue. In some embodiments, the eigenvalue can be plotted along with an EEG signal such that the user interface can provide an operator with a view of the EEG signal and also the trend of the eigenvalues.

In some embodiments, the user interface further includes a historical window of the EEG signal, the historical window of the EEG signal associated with the candidate seizure.

In some embodiments, the one or more circuits are configured to determine a moving window of eigenvalues of the EEG signal, determine that the eigenvalues are decreasing, and determine that the EEG signal is consistent with a candidate seizure based at least in part on the metrics in response to a determination that the eigenvalues are decreasing.

In some embodiments, the one or more circuits are configured to determine Renyi permutation entropy values (and/or any other types of entropy measures) based on the EEG signal, determine that the Renyi permutation entropy values are decreasing, and determine that the EEG signal indicates the candidate seizure in response to the determination that the eigenvalues are decreasing and a second determination that the Renyi permutation entropy values are decreasing.

In some embodiments, the one or more circuits are configured to determine Renyi permutation entropy values based on the EEG signal, determine that the Renyi permutation entropy values are increasing, determine sample entropy values based on the EEG signal in response to a first determination that the Renyi permutation entropy values are increasing, determine that the EEG signal indicates the candidate seizure in response to a second determination that the sample entropy values are decreasing (e.g., negative), and determine that the EEG signal does not indicate the candidate seizure in response to a third determination that the sample entropy values are increasing (e.g., positive).

Another implementation of the present disclosure is a method of seizure detection. The method includes receiving, by a processing circuit, an electroencephalogram (EEG) signal generated based on electrical brain activity of a patient, determining, by the processing circuit, metrics based on the EEG signal, the metrics indicating non-linear features of the EEG signal, determining, by the processing circuit, that the EEG signal indicates a candidate seizure by determining, based at least in part on the metrics, a change in the non-linear features of the EEG signal (e.g., in each of the non-linear features) over time, and generating, by the processing circuit, a seizure alert indicating that the EEG signal indicates the candidate seizure. The change in the non-linear features reflects a physiological force that gives rise to the candidate seizure.

In some embodiments, determining, by the processing circuit, that the EEG signal indicates the candidate seizure is based on at least one of a default parameter value or a user defined parameter value.

In some embodiments, the metrics include at least one of dimensionality, synchrony, Lyapunov exponents, entropy, global non-linearity, distance differences between recurrence trajectories, self-similarity, or eigenvalues.

In some embodiments, determining, by the processing circuit, that the EEG signal indicates the candidate seizure by determining, based at least in part on the metrics, the change in the non-linear features of the EEG signal over time by performing a preliminary analysis with one of the metrics, wherein the preliminary analysis indicates that the EEG signal indicates the candidate seizure or that the EEG signal includes noise and performing a secondary analysis with one or more metrics of the metrics to determine whether the EEG signal indicates the candidate seizure or that the EEG signal includes the noise.

In some embodiments, the method further includes determining, by the processing circuit, probabilities of a trajectory of each of the plurality of metrics at a plurality of points in time and determining, by the processing circuit, whether the trajectory of each of the plurality of metrics is significant based on the probabilities. In some embodiments, determining, by the processing circuit based at least in part on the plurality of metrics, the change in the non-linear features (e.g., a change in the trajectory of the non-linear features) of the EEG signal includes mapping significant metrics of the plurality of metrics to a category, wherein the category is a seizure category.

In some embodiments, the method includes determining, by the processing circuit, a dimensionality of the EEG signal by performing a phase space analysis by increasing a value of the dimensionality until a number of false neighbors reaches zero, wherein a starting value of the dimensionality is based on an age of the patient.

Another implementation of the present disclosure is a seizure detection system including one or more electrodes connected to a patient, the electrodes configured to generate an electroencephalogram (EEG) signal based on electrical brain activity of a patient. The system further includes a processing circuit configured to receive an electroencephalogram (EEG) signal generated based on electrical brain activity of a patient, determine metrics based on the EEG signal, the metrics indicating non-linear features of the EEG signal, determine that the EEG signal indicates a candidate seizure by determining, based at least in part on the metrics, a change in the non-linear features of the EEG signal (e.g., in each of the non-linear features) over time, and generate a seizure alert indicating that the EEG signal indicates the candidate seizure. The change in the non-linear features indicates a physiological force that gives rise to the candidate seizure.

In some embodiments, the processing circuit is configured to determine that the EEG signal indicates the candidate seizure based on at least one of a default parameter value or a user defined parameter value.

In some embodiments, the processing circuit is configured to determine that the EEG signal indicates the candidate seizure by determining a trajectory of a non-linear feature of the non-linear features by determining values of the non-linear feature over time, determining that a probability value of the trajectory is less than a probability level (e.g., a predefined critical probability level set by a categorization criteria) indicating that the occurrence of the trajectory is statistically significant, and determining that the EEG signal indicates the candidate seizure in response to a determination that the probability value of the trajectory is less than the probability level. In some embodiments, probability levels of the trajectories of multiple non-linear features are each compared to the probability level to determine that the trajectories are each statistically significant and/or whether the signal indicates the candidate seizure.

In some embodiments, each value of the values of the non-linear feature decreases with respect to a previous value of the values (i.e., each individual value of a pattern of values of the non-linear feature decreases relative to a prior value). In some embodiments, the processing circuit is configured to determine the probability value of the trajectory based on a number of the values each decreasing with respect to the previous value of the values (i.e., the number of consecutively decreasing values).

In some embodiments, the processing circuit is configured to receive user input via a user interface and determine the probability level by setting the probability level to a value selected by the user via the user input.

In some embodiments, the processing circuit is configured to retrieve a default value from a memory device of the seizure detection system and determine the probability level by setting the probability level to the default value retrieved from the memory device.

In some embodiments, the processing circuit is configured to determine that the EEG signal indicates the candidate seizure by determining a trajectory of each of the non-linear features by determining values of each of the non-linear features over time, determining that a probability value of the trajectory of each of the non-linear features is less than a probability level indicating that the occurrence of the trajectory of each of the non-linear features is statistically significant, and determining that the EEG signal indicates the candidate seizure in response to a determination that the probability value of the trajectory of each of the non-linear features is less than the probability level.

BRIEF DESCRIPTION OF THE DRAWINGS

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

DETAILED DESCRIPTION

Overview

Figure 1:
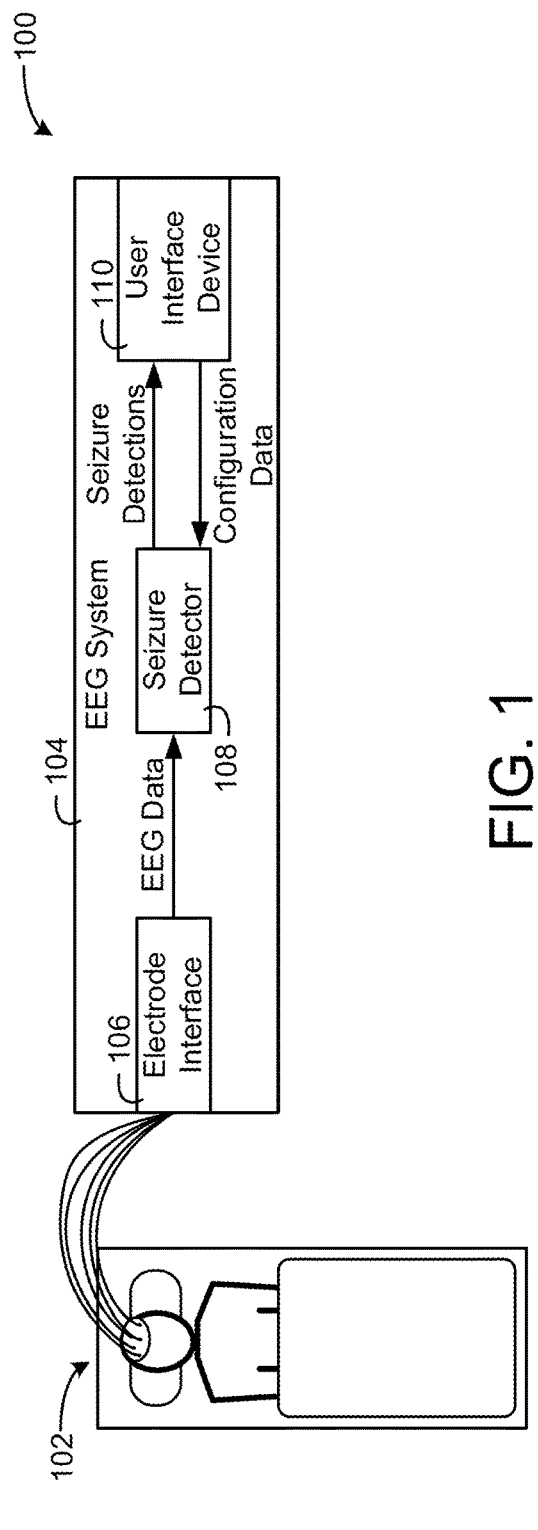
FIG. 1 is a block diagram of a local EEG system including a seizure detector for candidate seizure detection based on trends of non-linear features in an EEG signal, according to an exemplary embodiment.

Referring generally to the FIGURES, systems and methods for seizure detection based on changes in EEG non-linearities are shown, according to various exemplary embodiments. A seizure detector is configured to detect whether a candidate seizure is present in EEG data by analyzing changes in the non-linearities overtime, i.e., by detecting a change in non-linearities in the EEG data overtime (for example an increase), in some embodiments. The seizure detector is configured to analyze an EEG signal to determine whether there are epochs or events in the EEG signal which can be surfaced to a epileptologist or other clinical technician for manual review to definitively determine whether a candidate seizure has occurred, in some embodiments. The seizure detector can result in major time savings in the evaluation of patients undergoing EEG monitoring for seizure detection.

Rather than trying to detect the abnormal waveforms, e.g., a diverse set of morphologies of spikes and sharp waves in EEG data, the seizure detector can detect the physiologic forces which give rise to these abnormal waveforms. The seizure detector, configured to detect candidate seizures through non-linearities in some embodiments, out performs algorithms focused on a direct detection of abnormal waveform patterns, particularly when the patient is a child or an infant. In children and infants, the abnormal waveforms may be so varied and diverse, it may be difficult for the seizure detector to store an indication of each abnormal waveform. Rather than detecting particular abnormal waveforms, the seizure detector can detect the physiologic forces causing a candidate seizure by monitoring trends in the non-linearity in the EEG signal.

The seizure detector can utilize physiological or mathematical model(s) of the seizure process. Seizures arise from the abnormal interactions between groups of neurons (i.e., non-linear behavior). These interactions are in contrast to the apparent additivity or linear interactions present in many non-seizure states. Further, these interactions are dynamic in the sense that they evolve during the seizure. Hence, the development of a seizure reflects, or is driven by, an abnormal non-linear transformation between groups of nerve cells, which evolves with the evolution of the seizure. The branch of math which deals with this type of phenomena is called non-linear dynamic systems analysis.

In some embodiments, the seizure detection performed by the seizure detector can be utilized by (or integrated with) another system to operate closed loop stimulation devices dedicated to aborting seizures in a patient. Furthermore, in some embodiments, the seizure detector can be utilized to screen long-term historical records of patient EEG data. This can provide more rapid feedback to patients and caregivers that results in earlier interventions in seizures. Furthermore, the seizure detector can be utilized where trained epileptologists are not available for manual review of EEG signal data. The shortage of neurologist to review EEG signals is high within the United States and even higher outside the United States. It is estimated that nearly 200 pediatric intensive care units (ICUs) and 800 neonatal ICUs in the United States do not have adequately trained personnel to read EEG data.

Dependence upon visual cues (e.g., convulsion, changes in muscle tone, etc.) that a patient is seizing is fraught with problems. Observers (e.g., family members, nurses, technicians, etc.) often fail to detect a seizure in a patient through visible cues, often by as many as 30 to 40% of seizures are missed by observers. In part, this occurs since many seizures are non-convulsive and therefore more difficult to visually detect. Detecting a seizure through a visible cue is particular difficult in settings such as intensive care units where the ability of patients to communicate non-convulsive events (e.g., confusion, aphasia, visual, or other sensory disturbances is compromised) or where patients may be too young to communicate these events or may be paralyzed in the course of their illness. It is estimated that approximately 30 to 80% of seizures in an ICU may fall into one of these non-convulsive categories.

Nearly 85% of seizures in adults arise from the temporal lobes and generally involves the hippocampus. However, seizures in infants and children arise more diffusely from an anatomic perspective and their temporal morphology is much more diverse as compared to in adults. Hence, methodologies applied to adults, i.e., morphology based analysis, may not necessarily apply to children. Examples of morphology based analysis may include analysis of periodicity present in the EEG data. Often, as a seizure progresses, there is increasing amplitude of the EEG so analysis systems may analyze overall amplitude. Analysis of periodicity or amplitude indicate a build-up to a seizure. Other analysis algorithms may be linear time-domain analysis based on machine learning of a particular seizure pattern in a patient. A partial listing of these methods includes independent component analysis, morphological analyses, template matching, mimetic methods, parametric approaches, clustering techniques, and knowledge-based rules. However, such analysis may not be significantly successful in children. Instead, the non-linear trend analysis of the seizure detector described herein may be applied to children. Furthermore, such a non-linear trend analysis can also be applied to adults.

There is little uniformity in the clinical appearance of seizures in children. Some are without visible correlates, some are dramatic in appearance (e.g., drop attacks), while some include multiple behavioral components (e.g., Lennox-Gastaut Syndrome). Similarly, there are diverse electrographic patterns or features which are seen in pediatric seizures. There are the typical patterns of rhythmic build-up seen in adults, periods of voltage suppression (e.g., infantile spasms), "stop and start" patterns, high amplitude rhythmic slowing, bursts of polyspikes, etc. Multiple patterns can even be seen in a single patient. The effort to model or template match all of these patterns and transitions in patterns has not succeeded. Instead of using waveform morphology as the determinant of the mathematics of detection, the seizure detector described herein is configured to detect the form of the underlying physiological forces that produce these diverse changes, in some embodiments.

Furthermore, the same "driving function" can produce diverse outcomes depending upon the background EEG (reflecting dependence on initial condition). Since the moment to moment components of the EEG vary so enormously, the result of the action of a driving function on the variable input is a variable output, in some cases. The system behavior is a joint function of the form of the background activity, the form of the physiological force producing the state transition and any external variables (e.g. elevated temperature, presence of drugs, metabolic parameters, etc.). Obtaining the form of the driving function is easier during the brief periods of stationarity while determining its form during periods of transition is more challenging.

It should be noted that artifacts such as an electromyogram (EMG), movement, patting, electrode "popping" etc., should not have a preceding pattern of trajectory change like that seen in seizures. While the morphology of the observed artifact or other spurious waveforms can demonstrate visual similarity to seizures, these artifacts and other spurious events should not show the same pattern of physiological trajectory evolution seen in epilepsy. The seizure detector is configured to separate spurious events from seizure events to minimize false alarms, in some embodiments.

Seizure Detection

Referring now to FIG. 1, a system 100 including an EEG system 104 including a seizure detector 108 for candidate seizure detection based on trends of non-linear features is shown, according to an exemplary embodiment. In system 100, signal processing firmware and/or software are integrated into an EEG data acquisition system with and/or without additional signal processing boards to form the EEG system 104. The EEG system 104 is configured to collect EEG data from a patient 102 and further detect a candidate seizure (e.g., detect a potential candidate seizure for review by a user) based on the EEG data with the seizure detector 108, in some embodiments. The seizure detector 108 is a fully integrated parallel processor, in some embodiments.

A patient 102 is shown in FIG. 1 with multiple electrodes applied to the head of the patient 102. The electrodes sense electrical brain activity in the patient 102. The patient 102 may be a human, e.g., an adult, a teenager, a child, an infant, etc. Furthermore, the patient 102 may be an animal, e.g., a cat, a dog, a horse, a cow, etc. The number of electrodes applied to the patient 102 for collection of the EEG data for analysis by the seizure detector 108 may be determined by the desired precision of localization (when the focus is detection, accuracy of localization is less critical), the dimensions of the driving function determined by the seizure detector 108, the physical limits of the skull size, the spatial distribution of the electrodes, the spatial extent of the source and the correlation structure between the electrodes, etc.

The electrodes are connected to an electrode interface 106 included by the EEG system 104, in some embodiments. The electrode interface 106 can include one or more preliminary hardware circuits for generating the EEG data for analysis by the seizure detector 108. The hardware circuits may include amplifier circuits (e.g., differential amplifier circuits), filters (e.g., high-pass, low-pass, band-pass), analog to digital converters (ADCs), etc.

In some embodiments, the seizure detector 108 can be configured to analyze signals generated by a full set of electrodes applied to the patient 102 and/or analyze a subset of electrodes applied to the patient 102. In some embodiments, because dimensionality of a seizure does not generally exceed a value of four, approximately ten or less electrodes can be analyzed by the seizure detector 108 to detect a seizure. In this regard, even if a technologist applies a full set of electrodes, the seizure detector 108 can select the appropriate number of electrodes required (e.g., select ten electrodes).

In some embodiments, the seizure detector 108 is configured to determine a Lyapunov spectra which generally varies from about two to nine, with most seizures showing decreasing dimensions with seizure onset. During seizures it is unusual to see dimensions above four. Using multichannel EEG methods a trajectory can be characterized with 2d+1 electrodes where d is the estimated dimensionality of the underlying function with the Lyapunov spectra. The seizure detector 108 can, during operation, determine the dimensionality of the underlying function and cause user interface device 110 to recommend a particular number of electrodes for the patient 102. In this regard, the patient 102 may start with a predefined number of electrodes but, according to the analysis of the seizure detector 108, a technician may add additional electrodes to the patient 102 based on the determined dimensionality.

The EEG data may be representative of one or multiple EEG signals for brain activity of the patient 102. The seizure detector 108 can receive the EEG data and perform a non-linear analysis of the EEG data to detect whether the EEG data is indicative of a candidate seizure that has, will, or is occurring in the patient 102. The candidate seizure detections detected by the seizure detector 108 can be provided to the user interface device 110 for visual and/or audio notification for a user, e.g., a doctor, a nurse, a family member of the patient 102, an epileptologist, a technician, etc. Furthermore, via the user interface device 110, a user may provide configuration data. The configuration data may indicate the age of the patient 102, the weight of the patient 102, historical EEG data of the patient 102, medical conditions of the patient, etc. The non-linear analysis that the seizure detector 108 is configured to perform may be based, at least in part, on the configuration data.

The user interface device 110 may be a system or device configured to receive input from a user and/or provide output to the user. The user interface device 110 can be a monitor, e.g., a display screen. The display screen may be a light emitting diode (LED) screen, a Cathode ray tube display (CRT), a liquid crystal display (LCD) and/or any other type of display screen. The user interface device 110 may further include input devices, a mouse, a keyboard, a touch-screen, etc. Furthermore, the user interface device 110 may include a speaker for audio output, a microphone for audio input, etc. In some embodiments, the user interface device 110 is a computer, a smart phone, a tablet etc. in communication with the EEG system 104 and/or the seizure detector 108.

In principle, if a specific chain of events that leads to the emergence of a seizure are known, a system is configured to search for the specific chain of events, in some embodiments. For example, much is known about the abnormal electrical behavior of single neurons in the causative anatomic regions of seizures. For example, particularly temporal lobe seizures can be recognized in adults. However, seizures are caused by malfunctioning networks or assemblies of brain cells. Therefore, the seizure detector 108 can analyze a population of behaviors in search for driving forces behind seizure onset in the patient 102 instead of searching for a known morphological pattern (e.g., activity in particular areas of the brain, sharp spikes in activity, etc.). The forces behind the physiology of a seizure are not random. In fact, the forces are deterministic and can be detected by the seizure detector 108 by applying non-linear dynamic systems tools.

Figure 2:
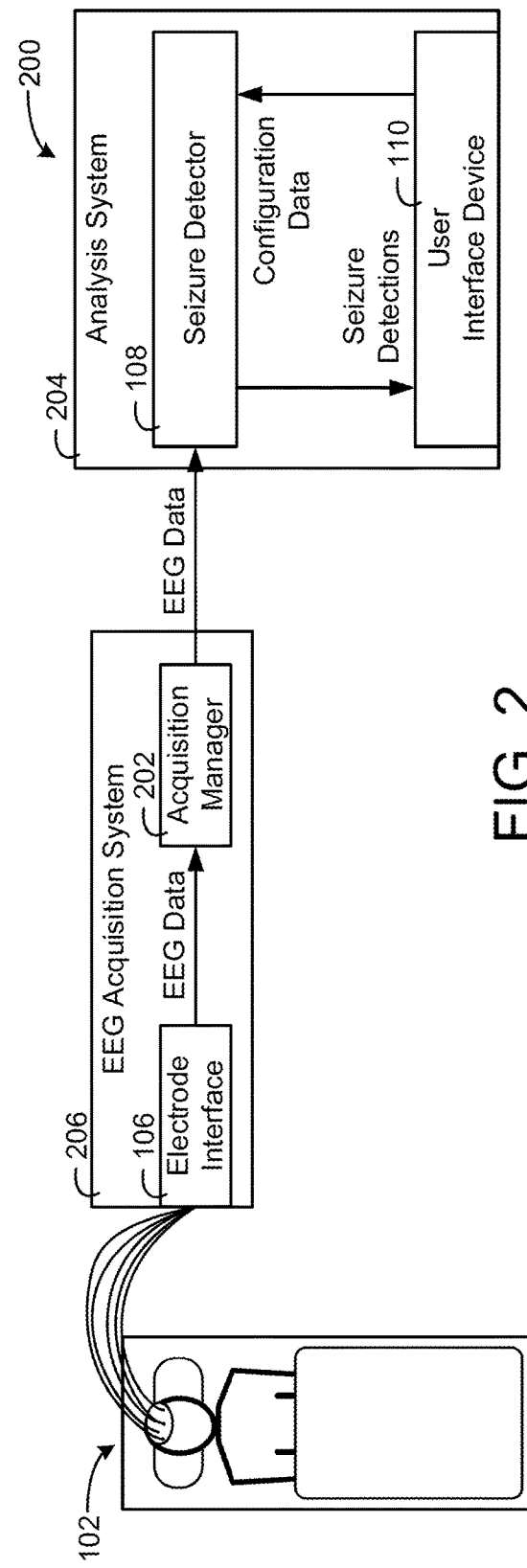
FIG. 2 is a block diagram of an EEG acquisition system for collecting EEG data and an analysis system including the seizure detector for analyzing the EEG data to detect a candidate seizure, according to an exemplary embodiment.
Figure 3:
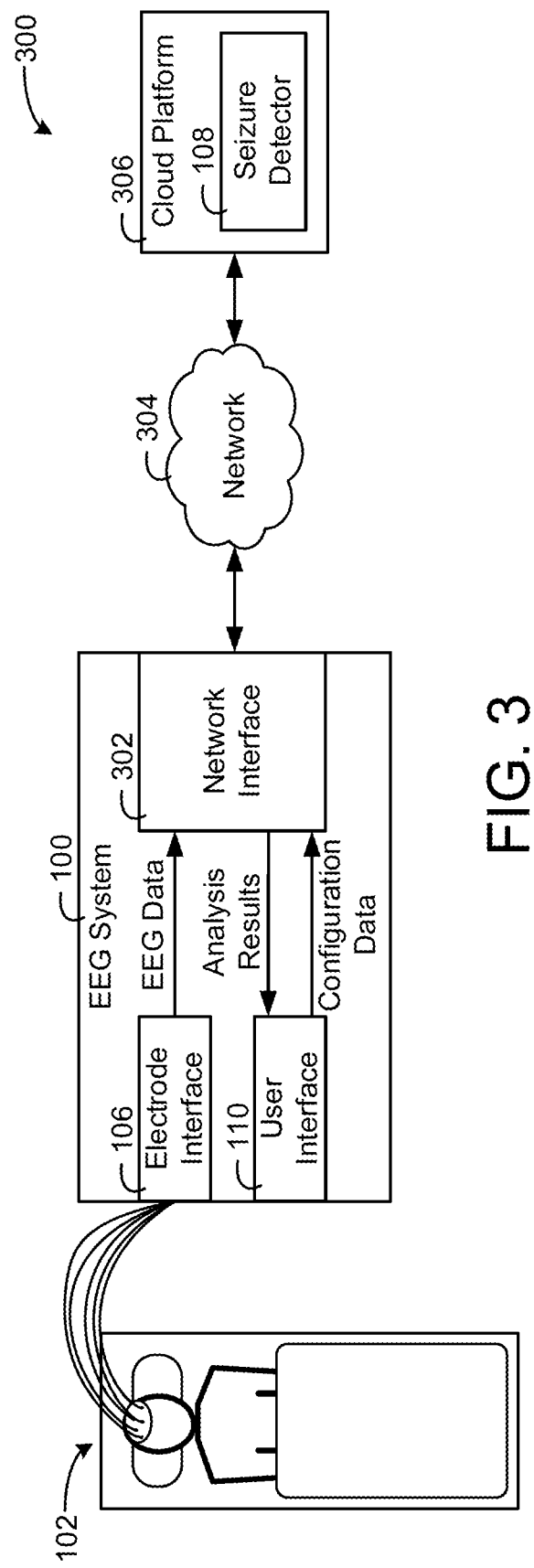
FIG. 3 is a block diagram of a remote cloud based system including the seizure detector for candidate seizure detection, according to an exemplary embodiment.

The seizure detector 108 is configured to apply seizure detection to any range of ages and can be performed in real-time, in some embodiments. Furthermore, the accuracy of the seizure detector 108 may be greater than 90% and less than double digit false positives in EEG data collected for the patient 102 over a 24 hour period. The seizure detector 108 can be implemented locally (as illustrated in FIGS. 1 and 2) and/or can be implemented remotely (as illustrated in FIG. 3).

In some embodiments, the seizure detector 108 is configured to select parameter values for detecting a seizure and/or categorizing an event performed by the seizure detector 108 based on user input (instead of, or in addition to, using default values programmed into the seizure detector 108). In some embodiments, the parameter values can be selected manually by a user, where the user provides user input via the user interface 110 associated with the seizure detector 108. The parameter values may be trajectory statistical significance level(s) and/or metric parameter values between component metrics when multiple metrics are simultaneously applied to a dataset. By selecting the parameter values based on the user input, false alarms generated by the seizure detector 108 can be reduced or a hit rate by the seizure detector 108 can be increased. Furthermore, by allowing a user to select the parameter values, the appropriate tradeoffs between false positives and true positives can be achieved by the seizure detector 108.

The user input can indicate a balance level (e.g., a weight) between decreasing false positives and increasing hit rates. This can be accomplished either by use of the suggested default values or by adjustment of the values, where the adjustment can be made based on personal preference or to best suit a particular patient situation. The balance level can be a value in a range and can correspond to lower or higher statistical significance levels (e.g., a balance level that favors decreasing false positives may be associated with lower probability values of a trajectory of a metric changing in a particular direction (increasing or decreasing) while a balance level that favors increasing hit rates may be associated with a higher probability value for the trajectory of the metric changing).

The seizure detector 108 is configured to detect shifting patterns of forces which produce the state transition from non-seizure to seizures without attempting to detect target waveform morphologies, in some embodiments. These abnormal physiological forces produce waveform trajectories that the seizure detector 108 is configured to quantify, in some embodiments. The seizure detector 108 can utilize the trajectories to detect multiple state changes, including seizure state changes, i.e., a change from a normal state in the patient 102 into a seizure state. More specifically, the seizure detector 108 is configured to determine one or multiple non-linear metrics based on EEG data which reflect the emergence of these trajectories, in some embodiments. The seizure detector 108 is configured to apply non-linear dynamic system tools to detect the emergence of these abnormal trajectories, in some embodiments.

The seizure detector 108 is configured to search for a seizure, in an EEG time series, by searching for a specific category of state change, in some embodiments. More particularly, the seizure detector 108 is configured to search for a change, i.e., an alteration to the structural non-linearities in the EEG data, in some embodiments. The seizure detector 108 is configured to apply non-linear methods to detecting the state changes in a mathematical state space, i.e., a starting point for the reconstruction of the systems dynamics (the dynamics of the brain activity of the patient 102).

The seizure detector 108 is configured to detect candidate seizures where there is a gradual and/or an abrupt transitions into the seizure state in the patient 102, in some embodiments. More particularly, the seizure detector 108 can apply dynamic systems analysis to detect both the abrupt changes, (e.g., bifurcations), along with many forms of gradual change. The search for a seizure is not a search for a specific isolated event nor a specific single value of a feature, instead, the seizure detector 108 can determine multiple non-linear metrics and track the non-linear metrics overtime to detect diagnostic shifts and patterns of changes in non-linear features of the EEG data. For example, the seizure detector 108 can determine whether a statistically significant increasing or decreasing trajectory of the non-linear features is occurring. For example, for a metric indicating non-linearity, seven sequential increasing values for the metric may be statistically significant to indicate that the trajectory is increasing. However, five sequential increases in the value of the metric may not be statistically significant to indicate an increasing trajectory. Similarly, the number of sequential decreasing values can be associated with a probability of occurring, e.g., five sequential decreasing values of the metric may not be significant while seven sequential decreasing values of the metric may be statistically significant.

For example, the probability that five sequential increasing values of a metric may be 0.032 (which can be determined by the seizure detector 108 from the five sequential increasing values and/or historical trajectory data). The probability that seven sequential increasing values of a metric may be 0.01. Because the probability that seven sequential increasing values is less than the probability that five sequential increasing values, seven sequential increasing values may be a greater statistical significance than five sequential increasing values (a lower probability level). A probability threshold could be applied by the seizure detector 108 to determine whether the increase or decrease of a metric is statistically significant, e.g., is the probability of the occurrence less than the probability threshold. Furthermore, the seizure detector 108 could apply a change number threshold, i.e., is the number of sequential increasing or sequential decreasing values greater than or equal to the change number threshold, i.e., if the threshold is seven, seven sequential increasing values of a metric are statistically significant while five sequential increasing values of the metric are not statistically significant.

The threshold for determining statistical significance can define the amount of false positives and missed seizure detections. For example, a threshold that requires a higher number of sequential increasing or sequential decreasing values may have less false positives but miss a high number of seizures. However, a lower value of the threshold may result in more false positives but miss less seizures. An optimization can be performed by the seizure detector 108 to properly set the thresholds for determining statistical significance. The optimization may attempt to minimize missing seizures and minimize false positives. The optimization can be based on user input, e.g., user feedback that identifies certain periods of a historical EEG signal as corresponding to a seizure or other periods of the EEG signal pertaining to a false positive.

The seizure detector 108 is configured to detect a change in the pattern of non-linear dynamics of the EEG data since the pattern of change is a constant aspect of the seizure state transition, in some embodiments. Often, the state changes in non-linearities precede, in time, the appearance of spikes, sharp waves or other visual signs in the EEG data of an electrographic or clinical seizure. Hence, the seizure detector 108 is configured to first determine a non-specific detector of changes in non-linearities from the EEG, i.e., eigenvalues, in some embodiments. If the non-specific detector indicates a candidate seizure, the seizure detector 108 can apply subsequent metric calculation and/or analysis. This allows the seizure detector 108 to save computational resources by applying low computational requirement calculation, e.g., eigenvalues, followed by higher computational requirement calculations, e.g., dimensionality.

Because of the potential instability of multiple non-linear measures, at small sample sizes, the seizure detector 108 is configured to apply a moving window for calculations of the metrics, in some embodiments. The particular values of the moving window duration and percent overlap within the window, may be predefined based on the specific metric, i.e., each metric may be associated with its own window duration and percent overlap. The greater the dependence of the particular metric upon sample size, to ensure stability of estimates, the seizure detector 108 is configured to determine the metric with a longer the window duration, in some embodiments.

The seizure detector 108 is configured to analyze changes in eigenvalues to detect a seizure, in some embodiments. However, changes in eigenvalues can arise from either quantitative changes in the ratio of linear to non-linear activity of the EEG data, or the presence of noise within the EEG data. Hence seizure detector 108 can determine and analyze multiple non-linear metrics together to detect a candidate seizure. For example, the seizure detector 108 is configured to determine entropy along with the eigenvalues to help make this distinction between a seizure and noise, in some embodiments. Noise often increases entropy, when the noise is not rhythmic, while most seizures decrease entropy.

The seizure detector 108 is configured to determine and analyze many other non-linear metrics, in some embodiments. The metrics that the seizure detector 108 is configured to analyze may be based on the configuration data, i.e., a clinical picture or syndrome of the patient 102 (e.g. drop attacks, infantile spasms, Lennox Gastaut Syndrome, post hypoxic encephalopathy, age, weight, etc.) and a baseline EEG pattern associated with the patient 102. The seizure detector 108 is configured to analyze the particular configuration data and determine and/or analyze the metrics appropriate for the patient 102, in some embodiments.

The clinical syndromes and the baseline EEG pattern (e.g., EEG patterns of normal brain activity, seizure patterns, etc.), the age of the patient, the weight of the patient, etc. can be included in the configuration data and can be utilized by the seizure detector 108 in the selection of the composition of the mixture (or a weighting of the mixture) of non-linear metrics in the second phase (and/or the preliminary phase). Candidate metrics include but are not limited to dimensionality, synchrony, Lyapunov exponents, various forms of entropy, global nonlinearity (via surrogate testing), distance differences between the recurrence trajectories in phase space, self-similarity, etc.

The output of the analysis performed by the seizure detector 108 may be a panel of non-linear values that change over time. Some of these patterns may be indicative of candidate seizures while other patterns reflect sleep onset and others, artifacts. Accordingly, the seizure detector 108 can map the panel of non-linear values to particular categories, e.g., seizure, noise, sleep, etc. The number of metrics in the panel may be set by the seizure detector 108 based on by the signal processing power of the hardware and/or firmware architecture of the EEG system. The selection of the metrics may change based on whether the seizure detector 108 is operating in a real-time mode where EEG data is being analyzed in real-time or in a historical analysis mode where previously recorded EEG data is analyzed.

Referring now to FIG. 2, a system 200 including an EEG acquisition system 206 for collecting EEG data and an analysis system 204 including the seizure detector 108 for analyzing the EEG data to detect a candidate seizure is shown, according to an exemplary embodiment. In the system 200, the signal processing hardware, firmware, and/or software of the seizure detector 108 is fully integrated into a stand-alone local computer separate from the EEG acquisition system 206, i.e., in the analysis system 204.

The analysis system 204 is configured to operate with the EEG acquisition system 206 using the output of the EEG acquisition system, i.e., the EEG data acquired by the EEG acquisition system 206, in some embodiments. The system 200 can be implemented in multiple embodiments, e.g., the analysis system 204 can be a screening device with a simplified head-box for the EEG acquisition system 206 and limited signal processing capabilities. The head-box could be structured to sit on top of an enclosure of the EEG acquisition system 206. The system 200 may be appropriate for warning and/or screening at a hospital or within a home of a patient. In some embodiments, the analysis system 204 is a plugin card (e.g., a circuit board configured with a connection port that can connect to a connection port of the EEG acquisition system 206). A user can insert the plugin card into the EEG acquisition system 206 to give the EEG acquisition system 206 all of the operational abilities of the analysis system 204. For example, the plug-in card can include a graphics or digital signal processing circuit and memory comprising instructions for implementing the operations described herein.

The EEG acquisition system 206 may include an acquisition manager 202. The acquisition manager 202 is configured to collect the EEG data and maintain a historical record of the EEG data. Furthermore, the EEG acquisition manager 202 can provide the EEG data to the analysis system 204 for analysis and seizure detection. Upon receiving a request from the analysis system 204, the acquisition manager 202 can provide the analysis system 204 requested historical EEG data that the acquisition manager 202 stores.

Referring now to FIG. 3, a system 300, a cloud-based implementation of the seizure detector 108 is shown, according to an exemplary embodiment. In the system 300, the seizure detection and associated signal processing is performed at a remote site, i.e., by a cloud platform 306. The cloud platform 306 may be one or more remote servers and/or local servers within a hospital, can be a cloud analysis system such as MICROSOFT AZURE, AMAZON WEB SERVICES, etc.

The EEG system 100 includes a network interface 302 which communicates the EEG data and/or the configuration data to the cloud platform 306 for analysis by the seizure detector 108 via a network 304. The network 304 can act as a pipeline between the EEG system 100 and the cloud platform 306 where the feature extraction and/or analysis is performed by the seizure detector 108. Results of the analysis performed by the analysis system 204 can be transmitted back to the EEG system 100 for display via the user interface device 110 and decision making by a user.

The network 304 can include one or multiple different wired and/or wireless networks. The networks may be a local area network (LAN) or a wide area network (WAN). The networks may be wired and include Ethernet wires, cables, and/or fiber optic connections and/or may be wireless and be Wi-Fi and/or cellular based networks. The network interface 302 can include one or more receivers, transmitters, transceivers, wireless radios, signal processing circuitry, etc. that the network interface 302 is configured to operate to communicate via the network 304, in some embodiments.

Figure 4:
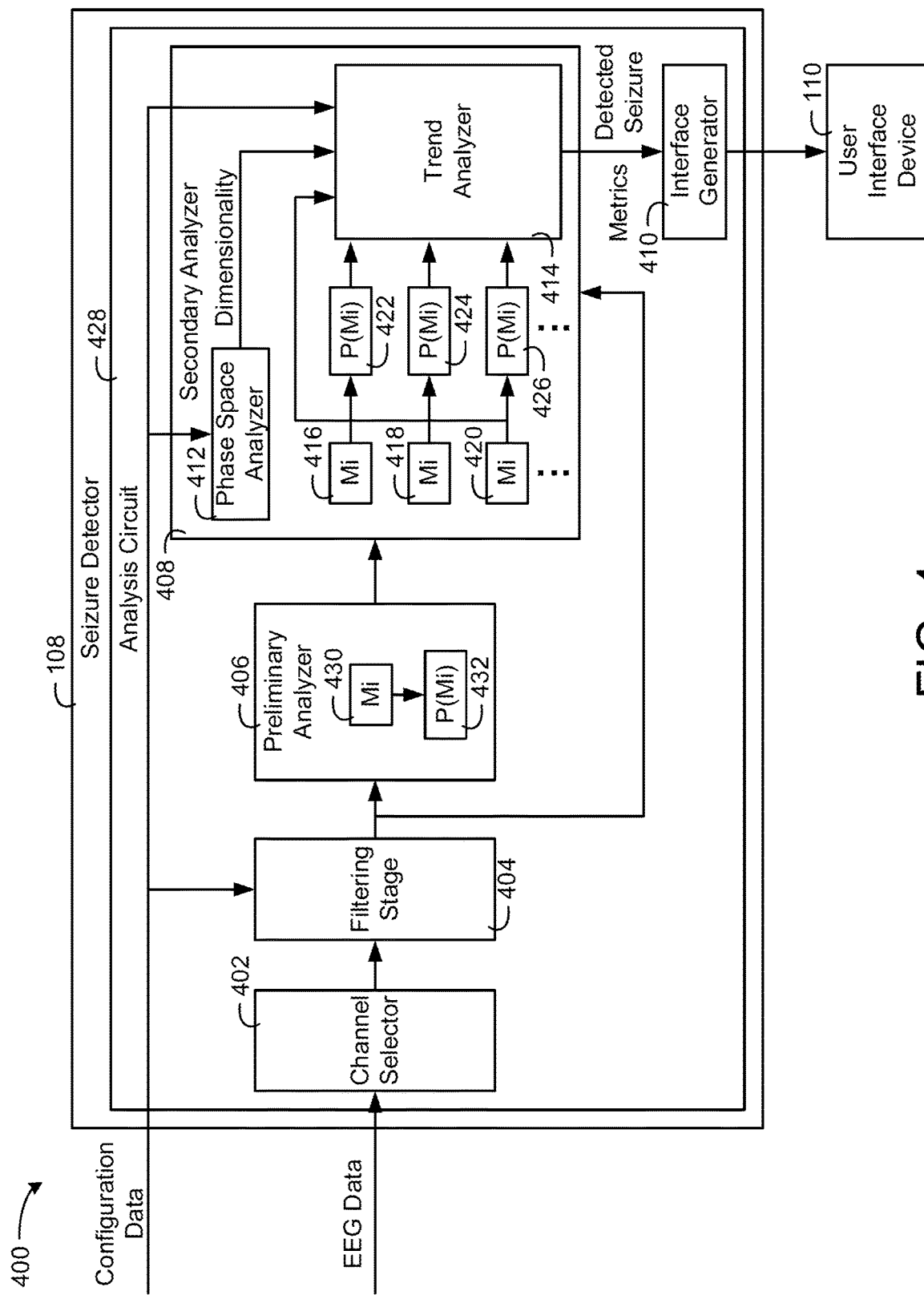
FIG. 4 is a block diagram of the seizure detector of FIGS. 1-3 shown in greater detail, according to an exemplary embodiment.

Referring now to FIG. 4, a system 400 including the seizure detector 108 is shown, according to an exemplary embodiment. The seizure detector 108 is shown to receive the configuration data and the EEG data. Furthermore, the seizure detector 108 is shown to output a user interface causing the user interface device 110 to display the user interface. The user interface may include indications of the presence of a candidate seizure and/or calculated metrics that the seizure detector 108 determines from the EEG data.

The seizure detector 108 includes an analysis circuit 428. The analysis circuit 428 can include one or more processing circuits for digital signal processing. The analysis circuit 428 can include field programmable gate arrays (FPGAs), application specific integrated circuits (ASICs), one or more central processing units (CPUs), one or more digital signal processing (DSP) units, one or more graphics processing units (GPUs), etc. There may be high processing requirements of the seizure detector 108 and the seizure detector 108 can apply shared computing across multiple processing units (e.g., separate processing cards, graphics cards, remote servers, cloud-based systems, etc.).

Furthermore, the analysis circuit 428 can include one or more memory devices. The memory devices can store instructions and/or computed data for execution on one or more processors. The memory devices can include random access memory (RAM), solid state drives (SSDs), hard disk drives (HDDs), FLASH memory, electrically erasable programmable read-only memory (EEPROM), and/or any other type of memory, either transitory or non-transitory.

The seizure detector 108 is configured to detect candidate seizures with an analysis of historical data and/or in a real-time analysis, in some embodiments. The seizure detector 108 is configured to detect a candidate seizure with less than fifteen seconds of delay between seizure onset and detection, in some embodiments. The seizure detector 108 is configured to detect a wide range of electrographic patterns (i.e., a mapping between types of seizures and an optimal detection algorithm performed by the seizure detector 108 for that type of seizure), in some embodiments. Furthermore, the seizure detector 108 is configured to separate seizure state transitions from artifacts and noise, in some embodiments. Furthermore, the seizure detector 108 is configured to detect several seizure types within the same patient, arising from several locations, again, within the same patient (multifocality), in some embodiments. The seizure detector 108 may have a true positive rate of more than 90% and a false positive rate of less than 8 false detections per day for a single patient.

A constant quantitative feature of the transition from the non-seizure to seizure state is a change in the contribution of non-linearities to the energy level of the signal. Many, and in adults most, transitions to the seizure state result in increased rhythmicity or increased synchronization between cellular groups. This is reflected in decreased eigenvalues (decreased contribution of linearities), decreased entropy, decreased dimensionality, and increased global nonlinearity, as revealed by surrogate testing. This pattern is not universal, however. The exceptions to this pattern are particularly notable in children and infants where existing algorithms fail. For example, in many patients with drop attacks the electrographic correlate is an initial brief burst of high energy slowing, followed by low voltage desynchronized activity. The temporal pattern of quantitative metrics would be more complex and show a period of increased entropy, increased eigenvalues and decreased global non-linearities. For this reason, the seizure detector 108 focuses on change in metrics rather than absolute values and utilizes multiple forms of change, to detect candidate seizures. This captures a wide range of ictal electrographic morphologies.

A challenge arises when the baseline EEG activity is poorly organized, has excessive slow wave activity, and is punctuated by high voltage sharp waves or spikes (e.g. Lennox-Gastaut Syndrome). In this case the baseline eigenvalue that the seizure detector 108 is configured to detect could be so low that the emergence of seizures may not be reflected in a drop of eigenvalues (e.g., a floor effect). In this instance the analysis with multiple metrics performed by the seizure detector 108 increases the likelihood of avoiding floor and/or ceiling effects. All of these changes can be distinguished from the intrusion of increased noise or artifacts (noise generally decreases eigenvalues and increases entropy).

The seizure detector 108 is configured to apply quantitative temporal change analysis to multiple metrics identifying a pattern of change across metrics which leads to the categorization of an event as a candidate seizure (e.g., a review alert), signal noise (no alert), or an uncertain classification (potential seizure alert occurs), in some embodiments. The seizure detector 108 can be adjusted to alter the trade-offs between true detections, false alarms, and misses by adjusting the significance levels of the probabilities required to be recognized as a significant change. The detections of the seizure detector 108 may be performed without utilizing machine learning. Machine learning requires a period of data acquisition with delayed therapy which may cause damage to a patient. In some embodiments, the temporal pattern of the metric trajectories can be subjected to post-processing (e.g., smoothing to remove transients) to decrease the variability in the application of the statistical criteria.

The analysis circuit 428 can apply a pipeline of analysis stages and can include a component configured to apply each stage. The components may be software modules, circuits, etc. The analysis circuit 428 includes a channel selector 402, a filtering stage 404, a preliminary analyzer 406, a secondary analyzer 408, and an interface generator 410. The EEG data received by the seizure detector 108 may first pass through the channel selector 402. The channel selector 402 may control which channels of the EEG data the seizure detector 108 performs analysis on. For example, where multiple electrodes are presents, one or more sets of electrodes may be appropriate for analysis by the analysis circuit 428. Accordingly, the channel selector 402 can select the appropriate EEG signal channels and provide the EEG signals of the selected channels to the filtering stage 404.

The filtering stage 404 can filter the EEG data with one or multiple low pass, high pass, and/or band-pass filters. The filters may be digital and/or hardware filters, for example, infinite impulse response (IIR) and/or finite impulse response (FIR) filters. The bandwidth appropriate for the signal analyzed by the analysis circuit 428 may be specific to the age of the patient 102. Accordingly, the filtering stage 404 may receive configuration data indicating a characteristic of the patient (e.g., age) and is configured to perform filtering based on the configuration data, in some embodiments.

The bandwidth that the filtering stage 404 passes may depend not only on the age of the patient but the metrics determined by the seizure detector 108 for detection of the candidate seizure. In some embodiments, the filtering stage 404 passes frequencies between 100 and 200 Hz. In some embodiments, the band of frequencies passed by the filtering stage 404 may be a range between 2 to 400 Hz.

The analysis circuit 428 is configured to determine multiple non-linear metrics and combine patterns of evolution of the multiple non-linear metrics together to detect a candidate seizure via the preliminary analyzer 406 and the secondary analyzer 408, in some embodiments. The preliminary analyzer 406 and the secondary analyzer 408 is configured to concatenate the application of several non-linear metric algorithms in a sequence and/or in parallel, in some embodiments. The seizure detector 108 can detect the presence of a candidate seizure through a first screening for non-specific global non-linear transformations, i.e., the metric 430 which may be eigenvalues. Furthermore, the secondary analyzer 408 is configured to process more computational intense metrics which focus on more specific types of non-linearities via the secondary analyzer 408, in some embodiments.

The preliminary analyzer 406 is configured to perform a screening stage by determining a moving window implementation of eigenvalues, e.g., the metric 430, in some embodiments. The eigenvalues decrease with the emergence of nonlinear interactions (e.g., seizures) or the appearance of noise. The eigenvalues increase when the EEG data becomes less rhythmic or periodic. Furthermore, the preliminary analyzer 406 is configured to determine whether the changes in the eigenvalues are statistically significant (e.g., have a significance value greater than a predefined amount or an probability of error less than a predefined amount) by determining the statistical significance 432 of the trend of the metric 430 such that only statistically significant changes in the eigenvalues are analyzed by the preliminary analyzer 406 to determine a candidate seizure, in some embodiments.

In some embodiments, the preliminary analyzer 406 determines the statistical significance with a moving window, i.e., determines trends of the metric 430 with a moving window similar to, or the same as, the moving window based trend analysis described with reference to the secondary analyzer 408. Over a particular window of samples of the metric 430, the preliminary analyzer 406 can determine whether the metric 430 is increasing or decreasing. With multiple windows, the preliminary analyzer 406 can determine a trend of the metric 430 and determine a probability level (the statistical significance 432) of the trend based on previous windows to increase or decrease over future windows.

In response to the preliminary analyzer 406 determining a decrease in the metric 430 by a statistically significant amount (e.g., the probability of an increase or decrease being less than a particular probability), the secondary analyzer 408 can calculate and analyze other metrics, i.e., the metrics 416-420. For example, the metrics 416-420 may include Renyi permutation entropy. The Renyi permutation may be determined by the secondary analyzer 408 on only the samples of the EEG data that the preliminary analyzer 406 detects statistically significant decreases in eigenvalues on. Permutation entropies may the computationally simplest and robust to noise and artifact. The secondary analyzer 408 is configured to further determine statistical significance of the metrics 416-420, i.e., determine the statistical significances 422-426 for the metrics 416-420, in some embodiments.

More specifically, each of the metrics 416-420, Mi, calculated by the secondary analyzer 408 may be time series of data. Based on the time series of the metrics 416-420, the secondary analyzer 408 is configured to determine statistical significances 422-426, P(Mi) that indicate the probability for a pattern of shifts of a trajectory of the metric under the null hypothesis, in some embodiments. Similarly, the statistical significances 422-426 can be time series. The trend analyzer 414 is configured to analyze a pattern of significant and non-significant values of the metrics 416-420 based on the statistical significances 422-426 across time, in some embodiments. A current set of significant metrics can be analyzed by the trend analyzer 414 as a group or panel of results. Each panel can be mapped to a particular category, e.g., a clinical category such as a candidate seizure event, no seizure, an indeterminate state, etc. Furthermore, the panels can map to other types of spurious events (non-seizures).

The metrics 416-420 may be many and varied, for example, there may be more than a dozen non-linear metric types described with many variants of each of these metric types. For example there are at least fourteen different forms of, or calculation methods for, entropy. The metrics 416-420 can include a loss of complexity metric. Each entropy metric may have performance advantages and disadvantages in specific settings (e.g., sample entropy performs better than most in detecting voltage suppression, Kolmogorov entropy is more vulnerable than multiple forms of permutation entropy which also have low computational complexity, etc.). Fuzzy entropy has an appeal in that class membership is graded so that the user has better control of the class boundaries. The frequency of the target events (seizures) can be included in the parameter values for some forms of entropy, for example tsalli entropy. Renyi entropy may be a better selection in instances in which state changes are frequent or profound (e.g., anesthesia). Information regarding the frequency of seizures, whether or not anesthesia is present, etc. can be included in the configuration data and thus the secondary analyzer 408 can determine and analyze an appropriate mixture of non-linear metrics. Examples of methodologies for calculating entropy can be found in Liang, Zhenhu, et al. "EEG Entropy Measures in Anesthesia." Frontiers in Computational Neuroscience, vol. 9, 2015, doi:10.3389/fncom.2015.00016, the entirety of which is incorporated by reference herein.

As described, the metrics 416-420 can be based upon and therefore derived from the EEG signal. One important aspect of the metrics 416-420 may be a trajectory over time of each of the metrics 416-420. The absolute values of the metrics 416-420 may vary enormously, as a function of patient age, state, syndrome, concomitant medications, etc. Therefore, the trend analyzer 414 is configured to analyze the trajectory of metrics 416-420, and not necessarily the absolute values of the metrics 416-420, to detect and/or classify candidate seizures. The direction of change in the metrics 416-420 over time caused by a candidate seizure (increase versus decrease) can vary based on patient age and/or the type of candidate seizure. For this reason, the secondary analyzer 408 is configured to determine the trajectories of the metrics 416-420 such that the trend analyzer 414 can determine, based on the trajectories, whether any segment of the EEG signal is indicative of a candidate seizure and/or should be surfaced for visual evaluation by an electroencephalographer.

The metrics 416-420 themselves also vary in terms of their stability and reliability, according to sample size. Sample size can be increased by increasing sample duration. However, an increased sample duration may risk missing a seizure event if the seizure event is shorter than the requisite sample duration. In some embodiments, the secondary analyzer 408 is configured to determine the direction of change of the metrics 416-420 by using moving windows.

For example, at a sampling rate of 400 Hz, a five second window that the secondary analyzer 408 can be configured to apply contains 2,000 samples. The step size and overlap for each of the windows applied to the metrics 416-420 by the secondary analyzer 408 can be user defined via the user interface device 110 and/or predefined. Typical values might be one second step sizes with four out of five samples overlapping between windows (i.e., four out of five samples being the same between two window positions for a window as the window moves).

Each window, when analyzed by the secondary analyzer 408, may indicate an increase or a decrease of the value of one of the metrics 416-420 and constitute the trajectory of the metric over time. The trend analyzer 414 may have statistical criteria for reviewing and/or analyzing a segment defined by one of the window positions of a window of one of the metrics 416-420. For example, assuming each sample is independent and behaves randomly, the probability of n consecutive changes in the same direction would be ½ to the $n^{th}$ power. In some embodiments, the secondary analyzer 408 is configured to determine the probabilities 422-426 for the patterns (increasing or decreasing) of the metrics 416-420. The probabilities may be probabilities that a predefined amount of changes will occur in one of the metrics 416-420 in a particular direction (e.g., a predefined amount of windows into the future will indicate increasing or decreasing values of the metrics based on the trajectories of previous windows). The trend analyzer 414 can apply threshold values which, if the probabilities rise above or fall below the threshold values, indicates that a particular one of the metrics 416-420 is increasing or decreasing at a statistically significant level. The trend analyzer 414 can apply one or more user defied and/or predefined thresholds to determine the statistically significant metrics 416-420 and/or map the statistically significant metrics 416-420 to a category, e.g., a seizure, noise, etc.

The selection of particular methods of calculating metrics performed by the secondary analyzer 408 may be dependent upon, the frequency of events, their spatial extent, the sample size, the dimension, the state of the patient 102, the seizure syndrome of the patient 102, the signal to noise ratio of the time epoch, all of which can be indicated through the configuration data or extracted by the secondary analyzer 408 from the EEG signal (e.g., signal to noise ratio). The calculation and mapping of metrics performed by the secondary analyzer 408 can take into signal and subject factors into account as well as the intrinsic computational complexity to determine which features should receive prioritization. This same process applies to the calculation of dimensionality, complexity (or loss of complexity), Lyapunov exponents, etc.

The metrics 416-420 and their statistical significances 422-426 can be passed into the trend analyzer 414 which can detect which trends in statistically significant metrics indicate a candidate seizure, noise, etc. For example, when the trend analyzer 414 detect that the Renyi permutation entropy increases determined by the secondary analyzer 408 along with the eigenvalues decreasing, the EEG data is indicative of noise or a burst suppression pattern of seizures in which case additional metrics should be analyzed. For example one of the metrics 416-420 may be sample entropy that the secondary analyzer 408, via phase space analyzer 412, determines in phase space. The sample entropy may be calculated by the secondary analyzer 408 after the calculation and analysis of the Renyi permutation entropy and/or may be calculated in parallel with the eigenvalues and/or Renyi permutation entropy. Calculation of the sample entropy may be less than a second delay.

Sample entropy may be more sensitive than permutation entropies to burst suppression. The trend analyzer 414 can determine whether the sample entropy is positive or negative and can classify the EEG data associated with the decreasing eigenvalues as noise if the sample entropy is positive. These results of the metrics 416-420 can be combined by the trend analyzer 414 to categorize the event. When both Renyi permutation entropy and eigenvalues decrease, the trend analyzer 414 can determine that the EEG data is indicative of a candidate seizure and the secondary analyzer 408 may not determine the Sample Entropy.

The phase space analyzer 412 is configured to perform a phase space analysis to determine metrics such as dimensionality, in some embodiments. The phase space analyzer 412 is configured to generate a phase space plot for the EEG signal, in some embodiments. Dynamical systems can be represented by a series of differential equations whose solutions may not exist in closed form. However, the phase space analyzer 412 can identify candidate seizure behavior by generating a trajectory in phase space. At each instance in a time series of the EEG signal, the phase space analyzer 412 is configured to generate a single point in phase space and a sequence of these points form a trajectory whose pattern provides insight into the nature of the driving function, i.e., insight into the presence or absence of a seizure, in some embodiments. The trajectories can occupy the entirety of the phase space or can converge to a lower dimensional region, called an attractor. The phase space trajectory of noise never converges. When adjacent points begin close to one another and then diverge, a strange attractor is said to exist and suggests the presence of chaotic behavior.

The phase space analyzer 412 is configured to perform the Takens method of time shift to generate a phase space plot based on empirical data of the EEG time series, in some embodiments. The Takens method is described in greater detail in Başar, Erol, et al. "Strange Attractor EEG as Sign of Cognitive Function." Machinery of the Mind, 1990, pp. 91-114., doi:10.1007/978-1-4757-1083-0_5. The EEG signal may be represented as the time-series, $$x(t_i), i=1, \ldots, N,$$

In some embodiments, from this time-series, the phase space analyzer 412 is configured to determine a phase space representation of the EEG signal with a time delay, td and an embedding dimension, m.

$$X(t_i)=[x(t_i), x(t_i+td), x(t_i+2td), \ldots, x(t_i+(m-1)td)]$$

The shape of the trajectory in phase space can be strongly influenced by the choice of the time lag, utilized by the phase space analyzer 412 to generate the phase space plot. In some embodiments, the time lag is the first zero in an autocorrelation function and is determined and then used by the phase space analyzer 412 to embed the signal in phase space. The phase space analyzer 412 is configured to apply one or multiple different methods for estimating the time lag. In some embodiments, the phase space analyzer 412 may determine the lag based on a non-linear metric that the phase space analyzer 412 is attempting to determine. In some embodiments, the estimators used by the phase space analyzer 412 to determine the lag are linear and/or non-linear.

The second value which is selected by the phase space analyzer 412 is the embedding dimension. If the dimension of the attractor is k, then the embedding theorem of Witney states that the embedding dimension must be 2k+1. Accordingly, the phase space analyzer 412 is configured to select the embedding dimension based on a known or determined dimension of the attractor, in some embodiments.

The phase space analyzer 412 is configured to estimate the dimension for phase space with the Cao method, in some embodiments. The dimension estimated by the phase space analyzer 412 may be a dimension of an attractor within the phase space. The phase space analyzer 412 is configured to start with a low dimension and successively increase the dimension until the number of false neighbors reaches zero, in some embodiments. The dimension reached by the phase space analyzer 412 can be linked to the presence or absence of a candidate seizure. For example, the trend analyzer 414 can determine, whether there is a candidate seizure based on the metrics 416-420 and/or based on the dimensionality determined by the phase space analyzer 412.

In some cases, the value of the dimension may be as low as one during a seizure. Furthermore, the dimension is usually below eight interictally. From a practical perspective, with this ascending method performed by the phase space analyzer 412, i.e., starting from a low dimension and increasing the dimension value, there can be a real-time compromise of performance based upon the computational burden of the ascending method. To overcome this computational burden, the phase space analyzer 412 can receive the configuration data which indicates the age of the patient. The phase space analyzer 412 is configured to select a starting dimension value based on the age of the patient to reduce the number of steps where the phase space analyzer 412 increments the dimensional value and determines when the number of false neighbors reaches zero, in some embodiments.

The starting dimensional value utilized by the phase space analyzer 412 in the ascending method may be lower for young children and greater in older children. This may be because the younger the age the lower the dimensionality, whether ictal or interictal. The selection of a starting dimension value may only be applied for young children, e.g., when the configuration data indicates the patient 102 is less than ten years old. There may be no clear difference in dimensionality between awake versus sleep in neonates and dimensionality age adjustments may be insignificant in older children and adults. The trend analyzer 414 may analyze trends in the dimensionality, not necessarily the absolute value of the dimensionality. For example, if the dimensionality falls overtime, the trend analyzer 414 can classify the EEG signal as indicating a candidate seizure. In this regard, the consequences of minor errors in the estimates of absolute values of dimensionality are partially decreased because classification of events is based upon changes in metrics, rather than absolute values.

The interface generator 410 is configured to generate an interface for display on the user interface device 110 based on the metrics determined by the preliminary analyzer 406 and/or the secondary analyzer 408, in some embodiments. Furthermore, the interface generator 410 is configured to generate the interface based on the presence of a candidate seizure as determined by the trend analyzer 414, in some embodiments. Furthermore, the user interface generated by the interface generator 410 may be based on user input, e.g., a request to display particular metrics, display historical EEG data, etc.

In some embodiments, the interface includes a trend of the EEG data in real-time. In some embodiments, the trend of the EEG data is displayed constantly. Furthermore, the interface generated by the interface generator 410 may include a superimposed graph of a trend of the eigenvalues determined by the preliminary analyzer 406 over the trend of the EEG. There may be a 750 millisecond delay between the eigenvalue and the EEG waveform. Every 750 milliseconds, the secondary analyzer 408 is configured to determine a new value of each of the metrics 416-420, in some embodiments. These values together form a trajectory for each of the metrics 416-420. Assuming that each value can only go up or down compared to the preceding value, the secondary analyzer 408 is configured to calculate the probability of n consecutive changes in the same direction, in some embodiments. If the secondary analyzer 408 detects eight consecutive changes in the same direction, this may indicate a sufficient probability of change in a particular direction. The secondary analyzer 408 may use six seconds of time to determine the probability of an increase or a decrease of the metrics 416-420 since each metric is determined over a 750 millisecond period and eight values may be determined in total to detect the increase or decrease. The preliminary analyzer 406 can be configured to perform the same processing for the metric 430.

When the changes in the eigenvalues become significant, the interface generator 410 is configured to cause the superimposed eigenvalue waveform to change color, in some embodiments. The interface generator 410 is configured to store the EEG trend time linked with the eigenvalue trend, in some embodiments. This allows a user to request, via the user interface device 110, a particular portion of historical EEG data. In response to the request, the interface generator 410 can cause the interface to display the requested portion of EEG data and the corresponding eigenvalue trend for that requested portion. In some embodiments, any section of EEG data, and the corresponding metrics determined for the section of EEG data, that is classified as a candidate seizure, is highlighted in the user interface generated by the interface generator 410. This can allow a trained clinician to review particular sections of EEG data that is possibly a candidate seizure and make a final determination regarding whether the section of data is indicative of a seizure.

In some embodiments, the interface generator 410 causes the interface to include a panel of the non-linear metrics determined by the secondary analyzer 408 that are statistically significant. The interface generator 410 can receive a user specified significance level via the user interface device 110 and cause the interface to include a particular non-linear metric in response to the statistical significance of the non-linear metric being greater than the user specified significance level for that metric.

In some embodiments, as a metric transitions from being non-significant to significant based on a threshold significance level and the statistical significance of each metric, the interface generator 410 causes the metric displayed in the interface to change from a first color to a second color, e.g., from black and white to yellow. When a pattern of a metric changes at a higher significance level (which can be defined based on a user setting or predefined parameters), the interface generator 410 can cause the metrics to become a third color, e.g., become blue. In some embodiments, the interface generator 410 displays a split screen of EEG data such that the EEG data is shown in a first window in real time and a period of historical EEG data that has been categorized as a candidate seizure is also displayed.

When there are no significant changes in the EEG trajectory, there may be no significance EEG data for review and the interface generator 410 can cause the interface to include an indication of no seizure. In some embodiments, the patterns and significance levels of the metrics may be user defined. In some embodiments, the patterns and/or significance levels may be predefined.

Figure 5:
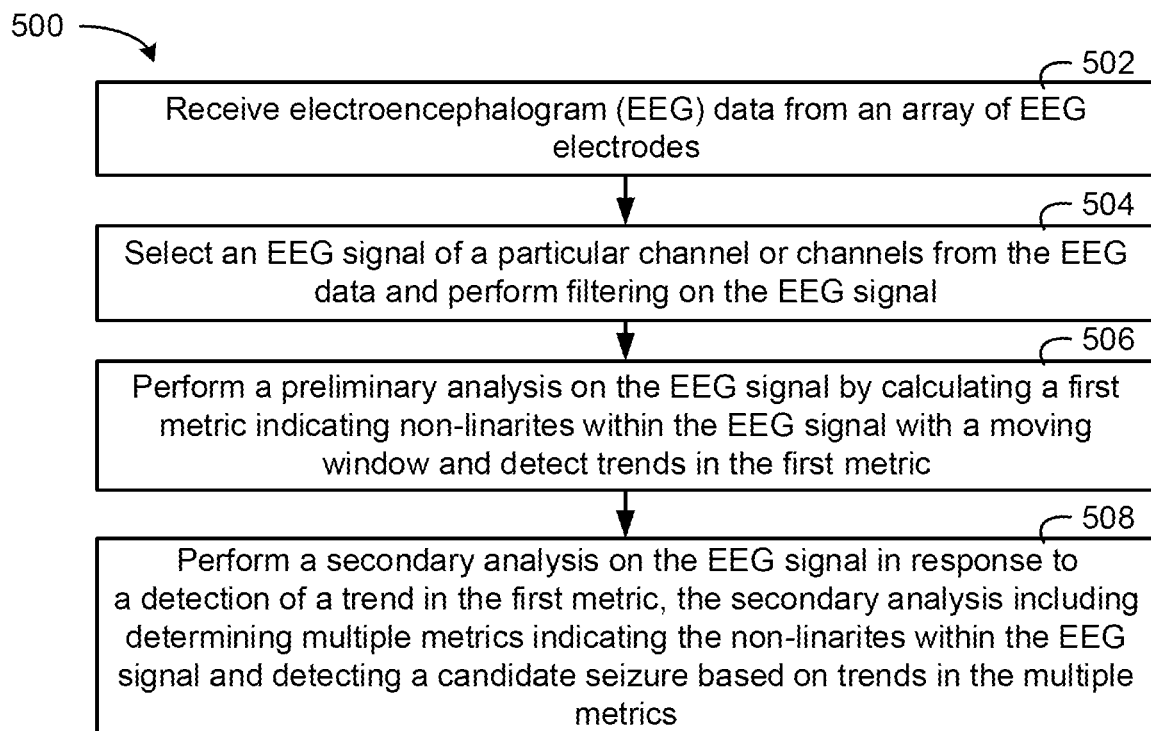
FIG. 5 is a flow diagram of a process of detecting a candidate seizure by determining changes of non-linear features of an EEG signal that can be performed by the seizure detector of FIG. 4, according to an exemplary embodiment.

Referring now to FIG. 5, a process 500 of detecting a candidate seizure by determining changes of non-linear features of an EEG signal is shown, according to an exemplary embodiment. The seizure detector 108 is configured to perform the process 500, in some embodiments. In particular, the channel selector 402, the filtering stage 404, the preliminary analyzer 406, and/or the secondary analyzer 408 of the seizure detector 108 are configured to perform some and/or all of the process 500, in some embodiments. Furthermore, any computing system or device as described herein can be configured to perform the process 500.

In step 502, the channel selector 402 receives EEG data from an array of EEG electrodes configured to sense brain activity of the patient 102. In some embodiments, the channel selector 402 receives the EEG data directly from the electrodes in real-time, i.e., as the data is collected. In some embodiments, the channel selector 402 receives the data after the data has been collected, i.e., from a database or other memory device storing the EEG data.

In step 504, the channel selector 402 can select an EEG signal of a particular channel or from multiple channels of the EEG data receive din the step 502. Furthermore, the filtering stage 404 can perform filtering on the EEG signal. In some embodiments, the selection of the channel includes selecting an EEG signal of particular electrode or group of electrodes from other EEG signals of other electrodes. In some embodiments, the selection performed by the channel selector 402 is predefined, i.e., the same channel is always selected. In some embodiments, the channel selection is selected based on configuration data, i.e., data indicating characteristics of the patient 102, e.g., age, height, medical syndromes, etc. The filtering may allow a particular range of frequencies to be passed. In some embodiments, the range of frequencies passed is predetermined. In some embodiments, the ranges of frequencies passed is also based on the configuration data.

In step 506, the preliminary analyzer 406 performs a preliminary analysis with a generalized metrics suited to detecting a shift in the ratio of non-linear versus linear contributors with a moving window. The preliminary analyzer 406 can detect trends in the metric. For example, the preliminary analyzer 406 may determine eigenvalues with a moving window and determine whether a trajectory of the eigenvalues is increasing or decreasing. The preliminary analyzer 406 may calculate probability values for the trajectory based on the values of the eigenvalues. If the probability values become small, i.e., less than a predefined amount, a statistical significance that the eigenvalue is increasing or decreasing can be identified by the preliminary analyzer 406 (e.g., the increase or decrease is statistically significant because the probability of the increase or decrease occurring is low).

A decrease in the eigenvalues may indicate a shift in the ratio of non-linear and linear contributors, i.e., an increase in the non-linear features of the EEG signal. In response to a detection of an increase in the non-linear features of the EEG signal in the step 506, the step 508 of the process 500 may be performed. If the non-linear features of the EEG signal are not increasing, the step 508 may be skipped so that computational resources are not utilized inefficiently.

In step 508, the secondary analyzer 408 performs a second analysis including determining metrics which will more precisely categorize the form of the non-linear change (e.g. changing dimensionality, entropy, degree of separation of the recurrence loops in phase space, Lyapunov exponents, etc.). The metrics analyzed the preliminary analysis (step 506) may be computationally efficient while the metrics analyzed in the second phase (step 508) may require greater computing resources, accordingly, processing the metrics in separate stages allows for use of computational resources only when necessary, i.e., only after the preliminary analysis indicates the possibility of a seizure. In the step 508, the secondary analyzer 408 can identify trends in the second metrics and, based on a particular pattern of changes in the second metrics, determine whether the EEG data indicates a candidate seizure or no seizure.

Figure 6:
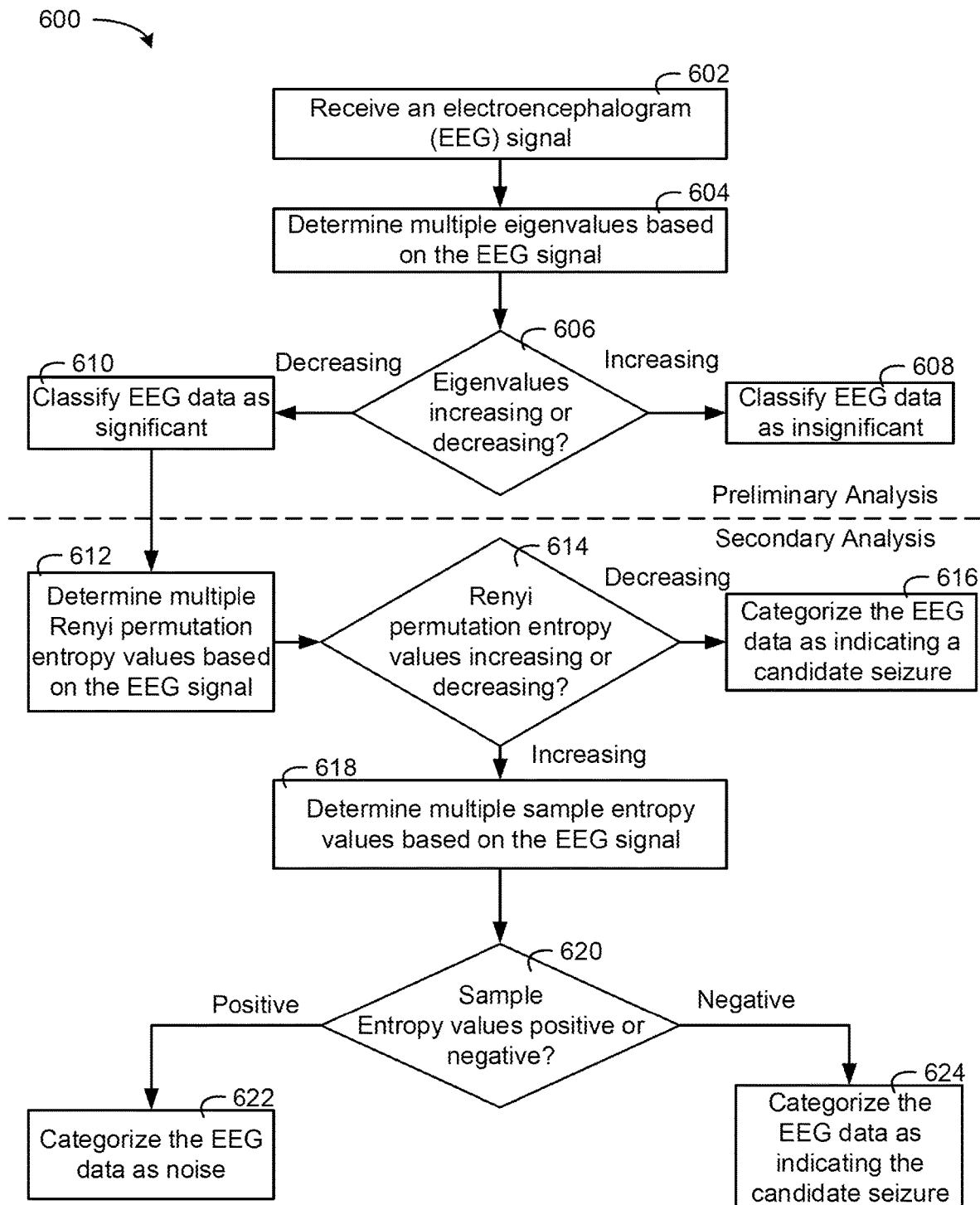
FIG. 6 is a flow diagram of a process of detecting a candidate seizure by determining changes of non-linear features of an EEG signal with eigenvalues, Renyi permutation entropy, and sample entropy that can be performed by the seizure detector of FIG. 4, according to an exemplary embodiment.

Referring now to FIG. 6, a process 600 of detecting a candidate seizure by determining changes of non-linear features of an EEG signal with eigenvalues, Renyi permutation entropy, and sample entropy is shown, according to an exemplary embodiment. The process 600 provides an exemplary metric analysis that the seizure detector 108 is configured to perform, in some embodiments. The decisions of the process 600 are exemplary, there may be many combinations of metrics and/or analysis rules that can be applied by the seizure detector 108 to detect a candidate seizure. The seizure detector 108 is configured to analyze various different patterns with various different non-linear metrics in addition to, or instead of, eigenvalues, Renyi permutation entropy, and/or sample entropy, in some embodiments. The seizure detector 108 is configured to perform the process 600, in some embodiments. In particular, the preliminary analyzer 406 and/or the secondary analyzer 408 of the seizure detector 108 are configured to perform some and/or all of the process 600, in some embodiments. Furthermore, any computing system or device as described herein can be configured to perform the process 600.

In step 602, the preliminary analyzer 406 can receive an EEG signal. The EEG signal may be a signal generated based on electrical brain activity of the patient 102. Furthermore, the EEG signal may be processed by the channel selector 402 and/or the filtering stage 404 before being received by the preliminary analyzer 406. The EEG signal may be a time series of data samples.

In step 604, the preliminary analyzer 406 can determine eigenvalues based on the EEG signal. In some embodiments, the preliminary analyzer 406 determines the eigenvalues with a moving window of eigenvalues. For example, the preliminary analyzer 460 can apply a window with a predefined length and a predefined overlap with a previous location of the window to generate an eigenvalue based on samples of the EEG signal falling within the window.

In step 606, the preliminary analyzer 406 can analyze a trend of the eigenvalues determined in the step 604 to determine whether the eigenvalue is increasing or decreasing over time. In some embodiments, the preliminary analyzer 406 determines a probability of a trajectory, i.e., an overall increase or decrease in the eigenvalues. If the probability of the trajectory to increase is greater than a predefined amount, the preliminary analyzer 406 performs the step 608. Similarly, if the probability of the trajectory to decrease is greater than a predefined amount, the preliminary analyzer 406 performs the step 610. If the eigenvalues do not demonstrate a significant increase or decrease, the preliminary analyzer 406 can classify the EEG data as insignificant.

If the eigenvalues are increasing, the preliminary analyzer 406 can classify the EEG data (particular samples of the EEG signal) indicating the increase as insignificant in step 608. However, if the preliminary analyzer 406 determines that the eigenvalues are decreasing, the data of the EEG signal can be classified by the preliminary analyzer 406 as significant and potentially indicating a candidate seizure, in step 610.

In step 612, the secondary analyzer 408 can determine Renyi permutation entropy values based on the EEG signal. In some embodiments, the secondary analyzer 408 determines the Renyi permutation entropy values for only segments of EEG data that the preliminary analyzer 406 has classified as significant. This may allow the secondary analyzer 408 to only perform calculations and utilize computational resources efficiently.

In step 614, the secondary analyzer 408 can analyze a trend of the Renyi permutation entropy determined in the step 612 to determine whether the Renyi permutation entropy is increasing or decreasing over time. In some embodiments, the secondary analyzer 408 determines a probability of a trajectory, i.e., an overall increase or decrease in the Renyi permutation entropy. If the probability of the trajectory is to increase is greater than a predefined amount, the secondary analyzer 408 performs the step 618. Similarly, if the probability of the trajectory is to decrease is greater than a predefined amount, the secondary analyzer 408 performs the step 616. If the Renyi permutation entropy does not demonstrate a significant increase or decrease, the secondary analyzer 408 can perform the step 618.

In step 618, the secondary analyzer 408 can determine sample entropy values based on the EEG signal. In some embodiments, the secondary analyzer 408 determines the sample permutation entropy values for only segments of EEG data that the preliminary analyzer 406 has classified as significant. This may allow the secondary analyzer 408 to only perform calculations, and utilize computational resources, when necessary. The sample permutation entropy may be determined by the secondary analyzer 408 with a moving window, in some embodiments.

In step 620, the secondary analyzer 408 determines whether the sample entropy is positive or negative. Based on the polarity of the sample entropy, the secondary analyzer 408 classifies the data as a candidate seizure, the step 624 when the sample entropy is negative, or as noise, the step 622 when the sample entropy is positive.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A seizure detection system comprising one or more circuits, the one or more circuits configured to:
   receive an electroencephalogram (EEG) signal generated based on electrical brain activity of a patient;
   determine a plurality of different types of metrics based on the EEG signal, the plurality of different types of metrics indicating non-linear features of the EEG signal, the plurality of different types of metrics including a dimensionality of the EEG signal;
   determine the dimensionality of the EEG signal by performing a phase space analysis by increasing a starting value of the dimensionality of the EEG signal until a number of false neighbors reaches zero, wherein the starting value of the dimensionality is based on an age of the patient;
   determine that the EEG signal indicates a candidate seizure based on the dimensionality;
   generate a seizure alert indicating that the EEG signal indicates the candidate seizure;
   generate a user interface, the user interface comprising:
      a real-time trend of the EEG signal; and
      the one or more of the plurality of different types of metrics; and
   cause a user interface device to display the user interface.

2. The seizure detection system of claim 1, wherein the seizure detection system is a cloud-based system, wherein the one or more circuits are configured to receive the EEG signal from a local EEG acquisition system via a network and provide result data to the local EEG acquisition system via the network.

3. The seizure detection system of claim 1, wherein the seizure detection system is a local system, wherein the local system is:
   integrated with a local EEG system; or
   connected locally to an EEG acquisition system.

4. The seizure detection system of claim 1, wherein the plurality of different types of metrics comprise at least one of synchrony, Lyapunov exponents, global non-linearity, distance differences between recurrence trajectories, entropy, or self-similarity.

5. The seizure detection system of claim 1, wherein the one or more circuits are configured to:
   determine probabilities of an occurrence of a pattern of a trajectory of each of the plurality of different types of metrics at a plurality of points in time;
   determine whether the probabilities of the occurrence of the pattern of the trajectory of each of the plurality of different types of metrics meet a predefined level of statistical significance based on the probabilities; and
   map metrics that meet the predefined level of statistical significance of the plurality of different types of metrics to a category, wherein the category is a seizure category.

6. A method of seizure detection comprising:
   receiving, by a processing circuit, an electroencephalogram (EEG) signal generated based on electrical brain activity of a patient;
   determining, by the processing circuit, a plurality of different types of metrics based on the EEG signal, the plurality of different types of metrics indicating non-linear features of the EEG signal, the plurality of different types of metrics including a dimensionality of the EEG signal;
   determining, by the processing circuit, the dimensionality of the EEG signal by performing a phase space analysis by increasing a starting value of the dimensionality of the EEG signal until a number of false neighbors reaches zero, wherein the starting value of the dimensionality is based on an age of the patient;
   determining, by the processing circuit, that the EEG signal indicates a candidate seizure based on the dimensionality;
   generating, by the processing circuit, a seizure alert indicating that the EEG signal indicates the candidate seizure;
   generating, by the processing circuit, a user interface, the user interface comprising:
      a real-time trend of the EEG signal; and
      the one or more of the plurality of different types of metrics; and
   causing, by the processing circuit, a user interface device to display the user interface.

7. One or more non-transitory storage medium storing instructions thereon, that, when executed by one or more processors, cause the one or more processors to:
   receive an electroencephalogram (EEG) signal generated based on electrical brain activity of a patient;
   determine a plurality of different types of metrics based on the EEG signal, the plurality of different types of metrics indicating non-linear features of the EEG signal, the plurality of different types of metrics including a dimensionality of the EEG signal;
   determine the dimensionality of the EEG signal by performing a phase space analysis by increasing a starting value of the dimensionality of the EEG signal until a number of false neighbors reaches zero, wherein the starting value of the dimensionality is based on an age of the patient;
determine that the EEG signal indicates a candidate seizure based on the dimensionality;
generate a seizure alert indicating that the EEG signal indicates the candidate seizure;
generate a user interface, the user interface comprising:
   a real-time trend of the EEG signal; and
   the one or more of the plurality of different types of metrics; and
cause a user interface device to display the user interface.

8. The one or more non-transitory storage medium of claim 7, wherein the plurality of different types of metrics comprise at least one of synchrony, Lyapunov exponents, global non-linearity, distance differences between recurrence trajectories, entropy, or self-similarity.

* * * * *